(12) United States Patent
Fujimura et al.

(10) Patent No.: US 6,436,920 B1
(45) Date of Patent: Aug. 20, 2002

(54) WRINKLING MODIFIERS

(75) Inventors: Tsutomu Fujimura; Noriko Ito; Minoru Nagai; Toshiya Ono; Akira Yamamuro; Yoshinori Takema, all of Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/934,837

(22) Filed: Aug. 23, 2001

Related U.S. Application Data

(63) Continuation of application No. 09/269,744, filed as application No. PCT/JP97/03604 on Oct. 8, 1997, now Pat. No. 6,306,848.

(30) Foreign Application Priority Data

Oct. 8, 1996 (JP) .............................................. 8-267015

(51) Int. Cl.[7] ........................... A01N 43/00; A61K 6/00; A61K 31/535
(52) U.S. Cl. ............... 514/210; 514/210.01; 514/228.8; 424/401
(58) Field of Search ........................... 514/210, 210.01, 514/228.8; 424/401

(56) References Cited

U.S. PATENT DOCUMENTS

| 5,589,178 A | 12/1996 | Aubert et al. | 424/401 |
| 5,723,133 A | 3/1998 | Nagai et al. | 424/401 |
| 5,939,078 A | 8/1999 | Fujimura et al. | 424/401 |

FOREIGN PATENT DOCUMENTS

| JP | 2-32006 | 2/1990 |
| JP | 2-42053 | 2/1990 |
| JP | 8-55340 | 2/1996 |

*Primary Examiner*—Michael G. Hartley
*Assistant Examiner*—Michael A. Willia
(74) *Attorney, Agent, or Firm*—Oblon, Spivak, McClelland, Maier & Neustadt, P.C.

(57) ABSTRACT

The invention relates to wrinkling modifiers and anti-aging cosmetic compositions which each comprise a guanidine derivative represented by the following general formula (1):

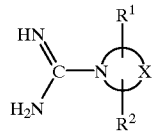

(1)

wherein

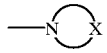

is a heterocyclic group selected from azetidine, pyrrolidine, piperidine, piperazine or morpholine, and $R^1$ and $R^2$ are the same or different from each other and independently a hydrogen atom, or an alkyl, hydroxyl, hydroxyalkyl, carboxyl, carboxyalkyl or amidino group, or a salt thereof. The cosmetic compositions are excellent in the effects of suppressing wrinkling and of removing wrinkles and give users a pleasant feeling upon use.

4 Claims, No Drawings

WRINKLING MODIFIERS

This application is a continuation of application Ser. No. 09/269,744 filed on Apr. 6, 1999, now U.S. Pat. No. 6,306,848 of International Application PCT/JP97/03604, filed on Oct. 8, 1997.

TECHNICAL FIELD

The present invention relates to wrinkling modifiers and anti-aging cosmetic compositions, and more particularly to anti-aging cosmetic compositions which are excellent in the effects of suppressing wrinkling and of removing or smoothing wrinkles.

BACKGROUND ART

It is a significant concern of, particularly, women to maintain the healthy and beautiful skin. However, the condition of the skin is always affected by factors such as humidity, ultraviolet rays, cosmetic compositions, aging, diseases, stress and eating habits. As the result thereof, various skin troubles such as the decrement of various functions of the skin and the aging of the skin occur. Of these, wrinkles occur due to dermal aging by aging, light aging by exposure to sunbeam, or the like. More specifically, cells f or producing fibers of the dermis are made small and lessened by exposure to sunbeam or with the increase in age. In particular, collagen fibers are lost to a great extent, and so the skin is aged by degeneration of the dermis, reduction of subcutaneous adipose tissue and the like, which forms the cause of wrinkling, relaxation, and loss of resilience.

Various compositions and methods have heretofore been proposed for preventing or treating the aging effects such as wrinkling [Japanese Patent Application Laid-Open Nos. 185005/1987, 502546/1987, 72157/1990, 288822/1990 and 41419/1995, Japanese Patent Application Laid-Open (KOHYO) No. 510542/1994 (through PCT route), etc.]. However, all of these proposals have not been fully satisfactory in the effect of modifying wrinkling (or preventing wrinkling and removing wrinkles). There has thus been a demand for development of cosmetic skin care compositions excellent in the effect of modifying wrinkling.

It is an object of the present invention to provide wrinkling modifiers and anti-aging cosmetic compositions which can solve the above-described problems, are excellent in the effects of suppressing wrinkling without impairing normal dermatophysiology and removing wrinkles, and give users a pleasant feeling upon use.

DISCLOSURE OF THE INVENTION

In view of the foregoing circumstances, the present inventors have carried out an extensive investigation with a view toward achieving the above object. As a result, it has been found that guanidine derivatives having a specific structure or acid-addition salts thereof are excellent in the effect of modifying wrinkling and give users a pleasant feeling upon use, thus leading to completion of the present invention.

According to the present invention, there are thus provided a wrinkling modifier and an anti-aging cosmetic composition, each comprising a guanidine derivative represented by the following general formula (1):

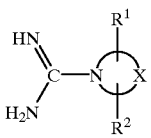

(1)

wherein

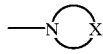

is a heterocyclic group selected from azetidine, pyrrolidine, piperidine, piperazine or morpholine, and $R^1$ and $R^2$ are the same or different from each other and independently a hydrogen atom, or an alkyl, hydroxyl, hydroxyalkyl, carboxyl, carboxyalkyl or amidino group, or a salt thereof.

According to the present invention, there is also provided a cosmetic skin care composition comprising the wrinkling modifier (1) and a synthetic sphingosine derivative represented by the following general formula (2):

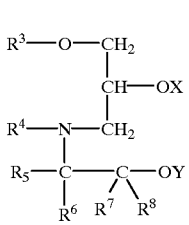

(2)

wherein $R^3$ is a linear, branched or cyclic, saturated or unsaturated hydrocarbon group having 4 to 40 carbon atoms, $R^4$, $R^5$, $R^6$, $R^7$ and $R^8$ are independently a hydrogen atom or a hydrocarbon group having 1 to 10 carbon atoms, which may be substituted by at least one hydroxyl group, and X and Y are independently a hydrogen atom or an alkyl group having 1 to 6 carbon atoms, which may contain at least one oxygen atom in its structure.

BEST MODE FOR CARRYING OUT THE INVENTION

Among the heterocyclic groups represented by

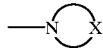

in the general formula (1) which represents the guanidine derivatives or the salts thereof used in the present invention, pyrrolidine, piperidine, piperazine and morpholine are preferred. The alkyl groups represented by $R^1$ and $R^2$ include linear or branched alkyl groups having 1 to 6 carbon atoms. Of these, alkyl groups having 1 to 4 carbon atoms are preferred. Specific examples of the alkyl groups include methyl, ethyl, n-propyl and isopropyl groups. Of these, methyl group is particularly preferred. The hydroxyalkyl groups include hydroxyalkyl groups having 1 to 6 carbon atoms, and hydroxyalkyl groups having 1 to 4 carbon atoms are preferred. Specific examples of the hydroxyalkyl groups include hydroxymethyl, hydroxyethyl and hydroxypropyl groups, with the hydroxymethyl and hydroxyethyl groups being particularly preferred. The carboxyalkyl groups include carboxyalkyl groups having 2 to 7 carbon atoms, and carboxyalkyl groups having 2 to 5 carbon atoms are preferred. Specific examples of the carboxyalkyl groups include carboxymethyl, carboxyethyl, carboxypropyl and carboxybutyl groups, with the carboxymethyl and carboxyethyl groups being particularly preferred.

$R^1$ and $R^2$ may be the same or different from each other and be an optional combination of 2 groups.

Stereoisomers exist in the guanidine derivatives (1) because of the presence of asymmetric carbon atoms. In the present invention, all these stereoisomers and mixtures thereof may be used.

Specific examples of the guanidine derivatives (1) include N-amidinoproline, 2-hydroxymethyl-1-pyrrolidinecarboxamidine, 3-hydroxy-1-pyrrolidinecarboxamidine, N-amidinoaziridine-2-carboxylic acid, N-amidino-2-piperidinecarboxylic acid, N-amidino-3-piperidinecarboxylic acid, N-amidino-4-piperidinecarboxylic acid, N-amidino-4-piperidinepropionic acid, pyrrolidinecarboxamidine, piperidinecarboxamidine, 2-methylpiperidinecarboxamidine, 3-methylpiperidinecarboxamidine, 4-methylpiperidinecarboxamidine, 2-methylmorpholinecarboxamidine, 3-methylmorpholinecarboxamidine, N-methyl-piperazinecarboxamidine, N-2-hydroxyethylpiperazine-carboxamidine and piperazinecarboxamidine.

An acid for forming salts of the guanidine derivatives (1) may be either an organic acid or an inorganic acid. Examples thereof include monocarboxylic acids such as formic acid, acetic acid, propionic acid, butyric acid, isobutyric acid, hexanoic acid, heptanoic acid, octanoic acid, nonanoic acid, decanoic acid, lauric acid, myristic acid, palmitic acid, stearic acid, acrylic acid, methacrylic acid, crotonic acid, isocrotonic acid, phenylacetic acid, cinnamic acid, benzoic acid, sorbic acid, nicotinic acid, urocanic acid and pyrrolidone-carboxylic acid; dicarboxylic acids such as oxalic acid, malonic acid, succinic acid, glutamic acid, adipic acid, pimelic acid, cork acid, azelaic acid, sebacic acid, maleic acid, fumaric acid, phthalic acid and terephthalic acid; hydroxy acids such as glycolic acid, lactic acid, malic acid, tartaric acid, citric acid and o-, m- or p-hydroxybenzoic acid; amino acids such as glycine, alanine, β-alanine, valine, leucine, phenylalanine, tyrosine, serine, threonine, methionine, cysteine, cystine, proline, hydroxyproline, pipecolic acid, triptophan, aspartic acid, asparagin, glutamic acid, glutamine, lysine, histidine, ornithine, arginine and aminobenzoic acid; lower alkylsulfonic acids such as methanesulfonic acid and trifluoromethanesulfonic acid; arylsulfonic acids such as benzenesulfonic acid and p-toluenesulfonic acid; hydrohalogenic acids such as hydrofluoric acid, hydrochloric acid, hydrobromic acid and hydriodic acid; and inorganic acids such as perchloric acid, sulfuric acid, nitric acacia, phosphoric acid and carbonic acid.

The guanidine derivatives (1) or the salts thereof can be obtained in accordance with, for example, a preparation process represented by the following reaction scheme:

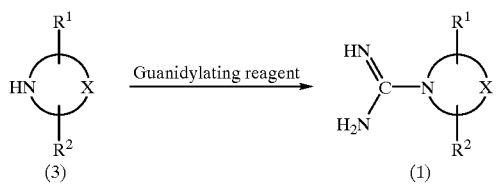

wherein

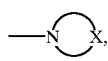

$R^1$ and $R^2$ have the same meanings defined above.

More specifically, a cyclic amine derivative (3) is reacted with a guanidylating reagent, whereby a guanidine derivative (1) or a salt thereof can be obtained.

Examples of the guanidylating reagent include known guanidylating reagents such as cyanamides, S-alkylisothioureas, O-alkylisoureas, aminoiminomethanesulfonic acid, 3,5-dimethyl-1-guanylpyrazole, 1H-pyrazole-1-carbamidine.

In the case where an S-alkylisothiourea, O-alkyl-isourea, 3,5-dimethyl-1-guanylpyrazole or 1H-pyrazole-1-carbamidine is used, the reaction may be conducted by stirring the reactants at 0 to 200° C. for 1 to 72 hours in the presence or absence of a base such as barium hydroxide, calcium hydroxide, magnesium hydroxide, sodium hydroxide, potassium hydroxide, lithium hydroxide, sodium hydrogen-carbonate, sodium carbonate, aqueous ammonia, a tertiary amine such as triethylamine, N,N-dimethylaniline, N,N'-dimethylpiperazine or N-methylpiperidine, or pyridine. In the case where a cyanamide is used, it is only necessary to stir the reactants at 0 to 200° C. for 1 to 72 hours, or stir the reactants at 25 to 200° C. for 1 to 72 hours in the presence of any one of the acids exemplified for the formation of the salts of the guanidine derivatives.

After completion of the reaction, as needed, the acid may be added to the reaction product in accordance with a method known per se in the art to isolate it as an acid-addition salt.

The guanidine derivatives (1) or the salts thereof may be used either singly or in any combination thereof. The amount of such a compound incorporated in the wrinkling modifiers and the cosmetic compositions is preferably 0.001 to 50% by weight. It is particularly preferred that it be incorporated in an amount of 0.001 to 30% by weight, more preferably 0.01 to 20% by weight, since the feeling upon use is improved, to say nothing of the wrinkling-modifying effect.

The synthetic sphingosine derivative is represented by the formula (2). Examples of the linear, branched or cyclic, saturated or unsaturated hydrocarbon group having 4 to 40 carbon atoms represented by $R^3$ in the general formula (2) include alkyl groups such as n-butyl, sec-butyl, pentyl, hexyl, octyl, 2-ethylhexyl, decyl, dodecyl, tetradecyl, pentadecyl, hexadecyl, octadecyl, 5,7,7-trimethyl-2-(1,3,3-trimethylbutyl)octyl, 2-heptylundecyl and methyl-branched isostearyl groups; alkenyl groups such as butenyl, hexenyl, oleyl, 9-octadecenyl, 9,12-octadeca-dienyl, 3,7-dimethylocta-2,6-dienyl and 3,7,11-trimethyl-2,6,10-dodecatrienyl groups; cycloalkyl groups such as cyclopentyl and cyclohexyl groups; and aryl groups such as phenyl, tolyl and naphthyl groups.

In the present invention, the linear or branched, saturated hydrocarbon groups having 4 to 40 carbon atoms are preferred. Of these, tetradecyl, octadecyl and methyl-branched isostearyl groups are particularly preferred.

The hydrocarbon groups having 1 to 10 carbon atoms represented by $R^4$ to $R^8$, which may be substituted by at least one hydroxyl group, include alkyl groups and mono-, di- or tri-hydroxyalkyl groups such as methyl, ethyl, n-propyl, isopropyl, hydroxymethyl, hydroxyethyl, 2-hydroxy-ethyl and 3,3,3-trihydroxypropyl groups. However, a hydrogen atom or methyl group is preferred as each of $R^4$ to $R^8$.

Examples of the alkyl groups having 1 to 6 carbon atoms represented by X and Y, which may contain at least one oxygen atom in their structures, include glucosyl, fructosyl, galactosyl, mannosyl, methyl, ethyl, propyl, hexyl, 2-hydroxyethyl, 3-hydroxyethyl, 4-hydroxypropyl, 5-hydroxy-6-hydroxybutyl, 2,3-dihydroxypropyl, 2-(1,2,3-trihydroxypropyl)methyl and 3-(2,3-dihydroxypropyloxy)-2-hydroxyethyl groups. However, a hydrogen atom or 2-hydroxyethyl group is particularly preferred as each of X and Y.

These sphingosine derivatives may be used either singly or in any combination thereof. The amount of such a derivative incorporated in the cosmetic compositions is preferably 0.0001 to 10% by weight. It is particularly preferred that it be incorporated in an amount of 0.001 to 2% by weight, since the feeling upon use is improved, to say nothing of the wrinkling-modifying effect.

Into the wrinkling modifiers and the cosmetic compositions according to the present invention, may be further incorporated an organic acid, an inorganic acid such as phosphoric acid, sulfuric acid or hydrochloric acid, or an ester thereof. The incorporation of such a compound is preferred because the wrinkling-modifying effect can be more enhanced.

No particular limitation is imposed on the organic acid or the ester thereof so far as it is not included in the guanidine derivatives (1). For example, α- or β-hydroxycarboxylic acids, dicarboxylic acids, fatty acids and esters thereof may be mentioned. One or more of these compounds may be incorporated. Examples of these organic acids include those represented by the following formulae (4) to (6), and esters thereof.

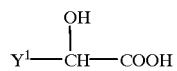

(4)

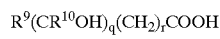

(5)

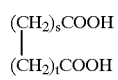

(6)

In the formula (4), $Y^1$ is a hydrogen atom or $CH_3(C_lH_m)_n$ (l being an integer of 1 to 27, m being an integer of 2 to 54, and n being 0 or 1). In the formula (5), $R^9$ and $R^{10}$ are independently a hydrogen atom, a saturated or unsaturated, branched, linear or cyclic alkyl group having 1 to 25 carbon atoms, an aralkyl group or an aryl group, q is an integer of 1 to 9, and r is an integer of 0 to 23. In the formula (6), s is an integer of 0 to 9, and t is an integer of 0 to 23. More specific examples of the organic acids include ascorbic acid, ε-aminocaproic acid, erythorbic acid, citric acid, succinic acid, tartaric acid, sorbic acid, dehydroacetic acid, lactic acid, urocanic acid, edetic acid, hydroxybenzonesulfonic acid, orotic acid, capric acid, glycolic acid, cerotic acid, nicotinic acid, hydroxyethanediphosphonic acid, phytic acid, fumaric acid, malic acid, levulinic acid, acrylic acid and oligomers or polymers thereof, and esters thereof.

Examples of the fatty acids include linolic acid, γ-linolenic acid, columbinic acid, icosa-(η-6,9,13)-trienoic acid, arachidonic acid, α-linolenic acid, thymunodonic acid, hexanoic acid, isostearic acid, undecylenic acid, stearic acid, palmitic acid, behenic acid, myristic acid, coconut oil fatty acid, lauric acid, lanolinic acid and DHA, and besides hydroxy fatty acids such as 12-hydroxystearic acid. The inorganic acids or the esters thereof include monoalkylphosphoric acids such as cetylphosphoric acid, and dialkylphosphoric acids.

In the present invention, among these organic acids and inorganic acids, the organic acids represented by the formulae (4), (5) and (6) are preferred. The dicarboxylic acids represented by the formula (6) are more preferred, with succinic acid being particularly preferred because the wrinkling-modifying effect can be more enhanced. The organic acid, inorganic acids and the like may be used either singly or in any combination thereof. The amount of such an acid incorporated in the wrinkling modifiers and the cosmetic compositions is preferably 0.001 to 30% by weight. It is particularly preferred that it be incorporated in an amount of 0.005 to 20% by weight, more preferably 0.01 to 10% by weight, since the feeling upon use is improved, to say nothing of the wrinkling-modifying effect. An incorporating ratio of the organic acid, inorganic acid or the like to the guanidine derivative or the acid-addition salt thereof is preferably 0.5:99.5 to 99.5:0.5 in terms of weight ratio. It is particularly preferred that the ratio be 5:95 to 95:5, since the wrinkling-modifying effect can be more enhanced.

Into the wrinkling modifiers and the cosmetic compositions according to the present invention, may be further incorporated an oily substance. No particular limitation is imposed on the oily substance, and examples thereof include hydrocarbons such as solid and liquid paraffins, crystal oil, ceresin, ozocerite, montan wax, squalane and squalene; ester oils such as olive oil, carnauba wax, lanolin, jojoba oil, glyceryl monostearate, glyceryl distearate, glyceryl monooleate, isopropyl stearate, neopentylglycol dicaprate and glycerol isostearate; higher alcohol such as cetanol and stearyl alcohol; and naturally extracted sphingosine derivatives and synthetic ceramide derivatives represented by the following general formula (7):

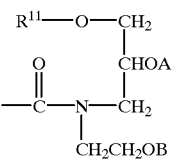

(7)

wherein $R^{11}$ is a linear or branched, saturated or unsaturated hydrocarbon group having 10 to 26 carbon atoms, $R^{12}$ is a linear or branched, saturated or unsaturated hydrocarbon group having 9 to 25 carbon atoms, and A and B are independently a hydrogen atom or a sugar residue. One or more of these oily substances may be used.

When these oily substances are incorporated, they are preferably incorporated in a proportion of 0.001 to 50% by weight, particularly preferably 0.005 to 30% by weight into the wrinkling modifiers and the cosmetic compositions.

Into the wrinkling modifiers and the cosmetic compositions according to the present invention, may be further incorporated a sterol. Examples of the sterol include cholesterol, provitamin $D_3$, campesterol, stegmastanol, stegmasterol, 5-dihydrocholesterol, α-spinasterol, palysterol, clionasterol, γ-sitosterol, stegmastenol, sargasterol, apenasterol, ergostanol, sitosterol, colubisterol, chondrillasterol, polyphellasterol, haliclonasterol, neospongosterol, fucosterol, aptostanol, ergostadienol, ergosterol, 22-dihydroergosterol, brassicasterol, 24-methylene-cholesterol, 5-dihydroergosterol, dehydroergosterol, fungisterol, cholestenol, coprostenol, zymosterol, 7-hetocholesterol, lathosterol, 22-dehydrocholesterol, β-sitosterol, cholestatrien-3β-ol, coprostanol, cholestanol, ergostenol, 7-dehydrocholesterol, 24-dehydrocholestadion-3β-ol, equilenine, equilin, estrone, 17β-estradiol, androst-4-ene-3 β,17β-diol and dehydroepiandrosterone. One or more of these sterols may be used.

When these sterols are incorporated, they are preferably incorporated in a proportion of 0.001 to 50% by weight, particularly preferably 0.005 to 30% by weight into the cosmetic skin care compositions.

Into the wrinkling modifiers and the cosmetic compositions according to the present invention, may be further incorporated a surfactant. Examples of the surfactant include polyoxyethylene alkyl ethers, polyoxyethylene fatty acid esters, polyoxyethylene sorbitan fatty acid esters, polyoxyethylene sorbitol fatty acid esters, glycerol fatty acid esters, polyoxyethylene hardened castor oil alkylsulfates, polyoxyethylene alkylsulfates, alkylphosphates, polyoxyethylene alkylphosphates, alkali metal salts of fatty acids, sorbitan fatty acid esters, glycerol fatty acid esters and alkyl glyceryl ethers. One or more of these surfactants may be used.

When these surfactants are incorporated, they are preferably incorporated in a proportion of 0.001 to 50% by weight, particularly preferably 0.005 to 30% by weight into the wrinkling modifiers and the cosmetic compositions.

Into the wrinkling modifiers and the cosmetic compositions according to the present invention, may be further incorporated a water-soluble polyhydric alcohol. Examples of the water-soluble polyhydric alcohol include alcohols having two or more hydroxyl groups in their molecules, for example, ethylene glycol, propylene glycol, 1,3-butylene glycol, 1,4-butylene glycol, dipropylene glycol, glycerol and polyglycerols such as diglycerol, triglycerol and tetraglycerol, glucose, maltose, maltitol, sucrose, fructose, xylitol, sorbitol, maltotriose, threitol, erythritol, and alcohols obtained by reduction of amylolytic sugar. One or more of these alcohols may be used.

When these water-soluble polyhydric alcohols are incorporated, their proportion in the wrinkling modifiers and the cosmetic compositions may be suitably determined according to the preparation forms of the modifiers and the cosmetic compositions. However, it is generally preferred to incorporate them in a proportion of 0.001 to 75% by weight, particularly preferably 0.1 to 25% by weight.

Into the wrinkling modifiers and the cosmetic compositions according to the present invention, may be further incorporated powder. Examples of the powder include extenders such as mica, talc, sericite, kaolin, nylon powder and polymethylsil sesquioxane; inorganic pigments such as pearl; organic pigments such as Red Color No. 202, Red Color No. 226, Yellow Color No. 4 and aluminum lake; and inorganic powders for ultraviolet screening, such as zinc oxide, titanium oxide, zirconium oxide and iron oxide. These powders may be subjected to a silicone treatment with methyl hydrogenmethylpolysiloxane, trimethylsiloxysilicic acid, methylpolysiloxane or the like, a fluorine treatment with a perfluoroalkyl phosphate, perfluoroalcohol or the like, an amino acid treatment with N-acylglutamic acid or the like, a lecithin treatment, a metal soap treatment, a fatty acid treatment, an alkylphosphate treatment, or the like before their use.

When these powders are incorporated, their proportion in the wrinkling modifiers and cosmetic compositions may be suitably determined according to the preparation forms of the modifiers and the cosmetic compositions. However, it is generally preferred to incorporate them in a proportion of 0.001 to 50% by weight, particularly preferably 0.005 to 30% by weight.

Into the wrinkling modifiers and the cosmetic compositions according to the present invention, may be further incorporated a silicone. No particular limitation is imposed on the silicone so far as it is that commonly incorporated into the classical cosmetic compositions. Examples thereof include octamethylpolysiloxane, tetradecamethylpolysiloxane, methylpolysiloxane, high-polymeric methylpolysiloxane and methylphenylpolysiloxane, and besides methylpolycyclosiloxanes such as octamethylcyclotetrasiloxane and decamethylcyclopenta-siloxane, trimethylsiloxysilicic acid, and modified silicones such as polyether alkyl-modified silicone and alkyl glyceryl ether-modified silicone.

When these silicones are incorporated, their proportion in the wrinkling modifiers and the cosmetic compositions may be suitably determined according to the preparation forms of the modifiers and the cosmetic compositions. However, it is generally preferred to incorporate them in a proportion of 0.001 to 50% by weight, particularly preferably 0.005 to 30% by weight.

Into the wrinkling modifiers and the cosmetic compositions according to the present invention, various ingredients commonly incorporated into the classical cosmetics, quasi-drugs, drugs and the like may be incorporated so far as no detrimental influence is thereby imposed on the objects of the present invention. Examples of such ingredients include inorganic salts such as magnesium sulfate, potassium sulfate, sodium sulfate, magnesium chloride and sodium chloride; viscosity modifiers such as polyvinyl alcohol, carboxyvinyl polymers, carboxymethyl cellulose, gelatin, tragacanth gum, xanthan gum, hyaluronic acid, tuberose extract, agarose and sodium alginate; and besides antiseptics such as parabens, pH adjusters, wetting agents, ultraviolet absorbents, coloring matter, medicinally-effective ingredients and perfume bases.

The wrinkling modifiers and the cosmetic compositions according to the present invention are preferably at a pH of 2 to 11. It is particularly preferred that the pH be at 3 to 10, since the normal physiological function of the skin can be retained. The wrinkling modifiers and the cosmetic compositions according to the present invention can be prepared in accordance with a method known per se in the art, formulated into any desired forms such as emulsions, dispersions, two-layer compositions, solutions and gel, and provided as toilet waters, milky lotions, creams, packs, paps, foundations and the like.

EXAMPLES

The present invention will hereinafter be described in more detail by the following examples. However, the present invention is not limited by these examples.

The following Compounds (1) to (16) were used as the guanidine derivatives or the salts thereof to evaluate them as to the wrinkling-modifying effect.

Compound (1): N-Amidino-trans-4-hydroxy-L-proline

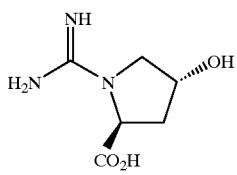

Compound (2): N-Amidino-L-proline

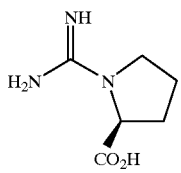

Compound (3): 3-Hydroxy-1-pyrrolidinecarboxamidine

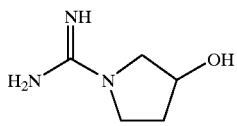

Compound (4): 2-Hydroxymethyl-1-pyrrolidinecarboxamidine

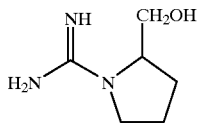

Compound (5): 4-Morpholinecarboxamidine

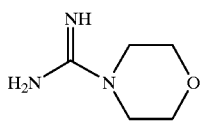

Compound (6): N-Amidino-4-piperidinecarboxylic acid

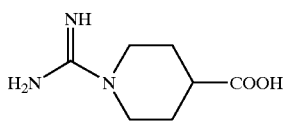

Compound (7): 1, 4-Piperazinedicarboxamidine

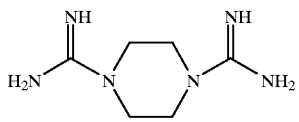

Compound (8): Succinic acid salt of Compound (3)

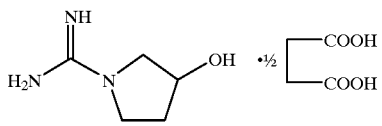

Compound (9): Succinic acid salt of Compound (4)

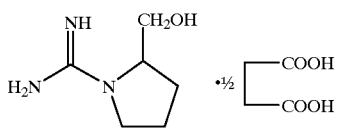

-continued

Compound (10): Succinic acid salt of Compound (5)

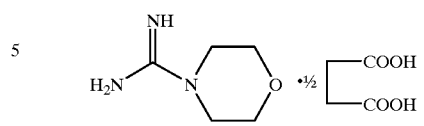

Compound (11): Succinic acid salt of Compound (7)

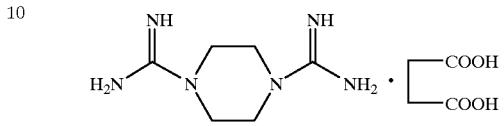

Compound (12): Glycolic acid salt of Compound (3)

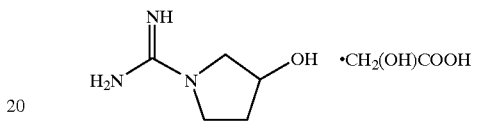

Compound (13): Glycolic acid salt of Compound (4)

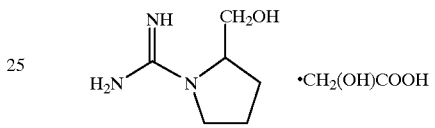

Compound (14): Pyrrolidinecarboxamidine

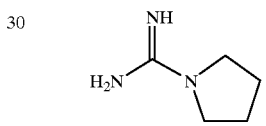

Compound (15): Piperidinecarboxamidine

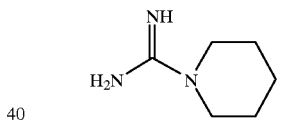

Compound (16): N-Amidino-4-piperidine acetic acid

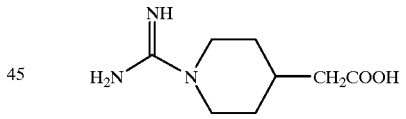

Effect of the Guanidine Derivatives (1) to (16) on Wrinkles Formed on Hairless Mice by Exposure to UVB (1) Hairless mice (HR/ICR, aged 6 weeks at the beginning of the experiment) were exposed to UVB 3 times a week by using 6 Toshiba healthy lamps, 20SE. The amount of energy was measured by means of a UV-Radiometer, UVR-305/365D manufactured by TOKYO OPTICAL K.K. The dose upon one exposure was determined to be 1 MED or less, i.e., 65 mJ in an amount of energy of 0.28 mW/cm$^2$. The exposure was effected for 20 weeks. After confirming that the hairless mice had got wrinkles at their backs, they were divided into groups each consisting of 8 mice. Aqueous ethanol (water/ethanol=50/50 vol. %) solutions separately containing Compounds (1) to (16) at a concentration of 4% were applied 5 times a week to their corresponding groups of mice over 6 weeks in a dose of 100 μl. As a control, aqueous ethanol (water/ethanol=50/50 vol. %) was applied in a dose of 100 μl like the samples. After completion of the application, the degree of wrinkles was visually observed to evaluate the samples in accordance with the following standard (wrinkle index). The results are shown in Table 1.

(Wrinkle index)

1: Wrinkles were completely removed or smoothed;

2: Wrinkles were scarcely observed;

3: Wrinkles were somewhat observed;

4: Wrinkles were observed to a great extent.

(2) In order to further analyze the particulars of wrinkles, skin replicas of the size of 14 mm in diameter were gathered from a portion of the back in each of the mice using a Hydrophilic Exaflex hydrophilic vinylsilicone impression material. Each of these replicas was held horizontally and illuminated at an angle of 30 degrees from the horizontal direction, thereby finding a proportion of shadows of the wrinkles as an area percent by means of an image analyzer. The results are shown in Table 1.

TABLE 1

| Compound | Wrinkle index | Area percent by image analysis (%) |
|---|---|---|
| Control | 3.73 | 10.6 |
| Compound (1) | 2.0 | 3.21 |
| Compound (2) | 2.125 | 2.48 |
| Compound (3) | 2.50 | 4.32 |
| Compound (4) | 2.50 | 5.37 |
| Compound (5) | 2.75 | 4.76 |
| Compound (6) | 2.75 | 3.51 |
| Compound (7) | 2.75 | 4.28 |
| Compound (8) | 2.25 | 3.26 |
| Compound (9) | 2.375 | 4.00 |
| Compound (10) | 2.50 | 3.41 |
| Compound (11) | 2.75 | 4.02 |
| Compound (12) | 2.50 | 3.62 |
| Compound (13) | 2.375 | 4.30 |
| Compound (14) | 2.125 | 3.62 |
| Compound (15) | 2.50 | 4.48 |
| Compound (16) | 2.25 | 4.25 |

As apparent from Table 1, the wrinkles formed on the backs of the hairless mice can be removed by applying any of the guanidine derivatives (1) to (16) thereto.

EXAMPLE 2

Compounds (17) to (21) in which the definitions of the respective symbols in the general formula (2) are as shown in Table 2 were used as the synthetic sphingosine derivatives to evaluate them as to the wrinkling-modifying effect in accordance with the same process as in Example 1. The experiment was conducted at concentrations of 5% for the guanidine derivatives and 0.5% for the synthetic sphingosine derivatives.

TABLE 2

| Compound | $R^3$ | $R^4$ | $R^5$—$R^8$ | X | Y |
|---|---|---|---|---|---|
| Compound (17) | Methyl-branched isostearyl | H | H | H | H |
| Compound (18) | Methyl-branched isostearyl | $CH_3$ | H | H | H |
| Compound (19) | Tetradecyl | H | H | H | H |
| Compound (20) | Octadecyl | $CH_3$ | H | H | H |
| Compound (21) | Methyl-branched isostearyl | H | H | —$CH_2$—$CH_2$—OH | H |

TABLE 3

| Guanidine derivative | Sphingosine derivative | Wrinkle index | Area percent by image analysis (%) |
|---|---|---|---|
| Not used | Not used | 3.75 | 10.2 |
| Compound (1) | Compound (17) | 2.25 | 3.73 |
| Compound (2) | Compound (17) | 2.75 | 4.03 |
| Compound (4) | Compound (17) | 2.75 | 3.88 |
| Compound (5) | Compound (17) | 1.75 | 2.40 |
| Compound (6) | Compound (17) | 2.125 | 2.39 |
| Compound (1) | Compound (18) | 2.5 | 3.60 |
| Compound (1) | Compound (18) | 2.75 | 3.97 |
| Compound (2) | Compound (19) | 2.375 | 3.45 |
| Compound (2) | Compound (19) | 2.125 | 3.26 |
| Compound (8) | Compound (20) | 2.25 | 4.14 |
| Compound (9) | Compound (21) | 2.0 | 2.78 |

As apparent from Table 3, the wrinkles formed on the backs of the hairless mice can be removed by the cosmetic skin care compositions comprising the guanidine derivative and the sphingosine derivative.

The following wrinkling-modifying cosmetic compositions were prepared.

| (Components) | (% by weight) |
|---|---|
| Example 3: Cream | |
| Stearic acid | 2.00 |
| Squalane | 2.00 |
| Cholesterol | 3.00 |
| Olive oil | 1.00 |
| Cetanol | 7.00 |
| Jojoba oil | 2.00 |
| Arginine 2-hexadecylphosphate | 2.00 |
| Polyoxyethylene (40 EO) hardened castor oil | 0.50 |
| Glycerol | 10.00 |
| 1,3-Butylene glycol | 5.00 |
| Compound (1) | 5.00 |
| Succinic acid | 1.00 |
| Purified water | Balance |
| Total | 100.00 |
| Example 4: Gel | |
| Polyoxyethylene (20 EO) isocetyl ether | 1.00 |
| Sodium polyoxyethylene (10 EO) trialkylphosphate | 1.00 |
| Sorbitol | 0.50 |
| 1,3-Propanediol | 0.50 |
| Xanthan gum | 0.50 |
| Tuberose polysaccharide | 3.00 |
| Carboxyvinyl polymer (Carbopol 940, product of Goodrich Co.) | 0.20 |
| Allantoin | 0.10 |
| Zinc sulfocarbolate | 0.20 |
| Compound (1) | 10.00 |
| Ethanol | 20.00 |
| Antiseptic | Proper amount |
| Perfume base | Proper amount |
| Purified water | Balance |
| Total | 100.00 |

| (Components) | (% by weight) |
|---|---|
| Example 5: Gel | |
| Silicone composition (XSG-16, product of Shin-Etsu Chemical Co., Ltd.) | 5.00 |
| Methylpolysiloxane (KF96A-6cs, product of Shin-Etsu Chemical Co., Ltd.) | 15.00 |
| Methylpolysiloxane (SH244, product of Dow Corning Toray Silicone Co., Ltd.) | 5.00 |
| Methylpolysiloxane.methyl(polyoxyethylene)-siloxane copolymer (SH3771C, product of Dow Corning Toray Silicone Co., Ltd.) | 2.00 |
| Methylpolysiloxane.methyl(polyoxyethylene)-siloxane copolymer (SH3775C, product of Dow Corning Toray Silicone Co., Ltd.) | 1.00 |
| Methyl cellulose | 0.20 |
| Hydroxyethyl cellulose hydroxypropyltrimethyl-ammonium chloride ether (Caticelo H-60, product of Kao Corporation) | 0.02 |
| dl-α-Tocopherol acetate | 0.05 |
| Isostearyl glycyrrhetinate | 0.10 |
| Isopropylmethylphenol | 0.10 |
| Zinc white | 1.50 |
| Compound (1) | 7.00 |
| Compound (17) | 0.50 |
| Ethanol | 5.00 |
| Antiseptic | Proper amount |
| Perfume base | Proper amount |
| Purified water | Balance |
| Total | 100.00 |
| Example 6: Toilet water | |
| Arginine | 0.40 |
| Lysine | 0.40 |
| Polyoxyethylene (40 EO) hardened castor oil | 1.50 |
| Methylpolysiloxane·methyl(polyoxyethylene)-siloxane copolymer (SH3775C, product of Dow Corning Toray Silicone Co., Ltd.) | 0.60 |
| Glycerol | 5.00 |
| Glycinebetaine | 0.20 |
| Trisodium citrate | 0.90 |
| Citric acid | 0.40 |
| Urea | 0.50 |
| ε-Aminocaproic acid | 0.10 |
| Compound (1) | 5.00 |
| Compound (17) | 0.50 |
| Ethanol | 5.00 |
| Antiseptic | Proper amount |
| Perfume base | Proper amount |
| Purified water | Balance |
| Total | 100.00 |
| Example 7: Toilet water | |
| Triethanolamine | 0.40 |
| Potassium hydroxide | 0.20 |
| Polyoxyethylene (20 EO) isocetyl ether | 0.30 |
| Sodium polyoxyethylene (8 EO) oleyl ether phosphate | 0.30 |
| Sodium polyoxyethylene (10 EO) dialkyl-phosphate | 0.10 |
| Polyethylene glycol 1500 | 2.00 |
| Polyoxyethylene (10 EO) methylglycoside | 1.50 |
| Dipropylene glycol | 0.50 |
| Disodium hydrogenphosphate | 0.50 |
| Succinic acid | 0.30 |
| Compound (1) | 7.00 |
| Ethanol | 10.00 |
| Antiseptic | Proper amount |
| Perfume base | Proper amount |
| Purified water | Balance |
| Total | 100.00 |

| (Components) | (% by weight) |
|---|---|
| Example 8: Pack | |
| Polyvinyl alcohol (Gohsenol EG-30, product of The Nippon Synthetic Chemical Industry Co., Ltd.) | 15.00 |
| Aqueous solution of carboxymethylchitin (Chitin Liquid HV-10, product of Ichimaru Pharcos Co., Ltd.) | 5.00 |
| Triglucopolysaccharide (Pullulan PI-20, product of Hayashibara Company, Ltd.) | 0.50 |
| Xanthan gum | 0.50 |
| Sodium carboxymethyl cellulose | 0.50 |
| Titanium oxide | 15.00 |
| Aluminum magnesium silicate | 1.00 |
| 1-Isostearoyl-3-myristoylglycerol | 1.00 |
| Diglycerol | 1.50 |
| Polyoxyethylene (20 EO) isocetyl ether | 1.00 |
| Compound (1) | 7.00 |
| Compound (14) | 0.70 |
| Ethanol | 5.00 |
| Antiseptic | Proper amount |
| Perfume base | Proper amount |
| Purified water | Balance |
| Total | 100.00 |
| Example 9: Milky lotion | |
| Palmitic acid | 0.50 |
| Olive oil | 2.00 |
| Cetanol | 1.00 |
| Jojoba oil | 5.00 |
| Sodium monohexadecylphosphate | 2.00 |
| Sorbitan monostearate | 0.50 |
| Glycerol | 15.00 |
| Ethanol | 5.00 |
| Compound (2) | 10.00 |
| Compound (17) | 0.30 |
| Lactic acid | 2.00 |
| Purified water | Balance |
| Total | 100.00 |
| Example 10: Milky lotion | |
| N-(3-Hexadecyloxy-2-hydroxypropyl)-N-2-hydroxyethyldecanamide | 0.50 |
| N-(3-Hexadecyloxy-2-hydroxypropyl)-N-2-hydroxyethylhexadecanamide | 1.00 |
| N-(3-Tetradecyloxy-2-hydroxypropyl)-N-2-hydroxyethyldecanamide | 0.50 |
| Polyoxyethylene (10 EO) hardened castor oil | 1.00 |
| Methylpolysiloxane.methyl(polyoxyethylene)-siloxane copolymer (SH3775C, product of Dow Corning Toray Silicone Co., Ltd.) | 1.00 |
| Sorbitan monostearate | 0.20 |
| Sodium stearoylmethyltaurine | 0.50 |
| Cholesterol | 0.80 |
| Cholesterol isostearate | 0.20 |
| Stearic acid | 0.20 |
| Palmitic acid | 0.30 |
| Myristic acid | 0.10 |
| Pentyl glycol dicaprate | 4.00 |
| Methylpolysiloxane (KF96A-500cs, product of Shin-Etsu Chemical Co., Ltd.) | 2.00 |
| Isostearyl alcohol | 1.20 |
| Cetyl alcohol | 1.00 |
| Glycerol | 3.50 |
| Lactic acid | 0.20 |
| Sodium lactate | 0.30 |
| Compound (2) | 5.00 |
| Antiseptic | Proper amount |
| Perfume base | Proper amount |
| Purified water | Balance |
| Total | 100.00 |

-continued

| (Components) | (% by weight) |
|---|---|
| Example 11: Pap | |
| α-Monoisostearyl glyceryl ether | 1.00 |
| Pentyl glycol neocaprate methylpolysiloxane | 4.00 |
| Glycerol | 35.00 |
| Purified water | 15.80 |
| Sodium polyacrylate | 5.50 |
| Aluminum potassium sulfate | 1.00 |
| Aqueous solution (10%) of polyacrylic acid | 15.00 |
| Precipitated silicic acid anhydride | 2.00 |
| Compound (1) | 10.00 |
| Compound (17) | 0.20 |
| Purified water | Balance |
| Total | 100.00 |

Industrial Applicability

The wrinkling modifiers and the cosmetic compositions according to the present invention are excellent in the effects of suppressing wrinkling and of removing wrinkles and give users a pleasant feeling upon use.

What is claimed is:

1. A cosmetic skin care composition comprising i) a wrinkling modifier comprising a guanidine derivative represented by the following general formula

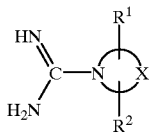
(1)

wherein

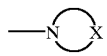

is a heterocyclic group selected from azetidine, pyrrolidine, piperidine, piperazine or morpholine, and $R^1$ and $R^2$ are the same or different from each other and independently a hydrogen atom, or an alkyl, hydroxyl, hydroxyalkyl, carboxyl, carboxyalkyl or amidino group, or a salt thereof; and ii) a synthetic sphingosine derivative represented by the following general formula (2):

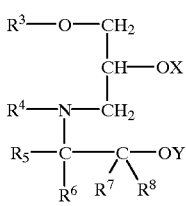
(2)

wherein $R^3$ is a linear, branched or cyclic, saturated or unsaturated hydrocarbon group having 4 to 40 carbon atoms, $R^4, R^5, R^6, R^7$ and $R^8$ are independently a hydrogen atom or a hydrocarbon group having 1 to 10 carbon atoms, which may be substituted by at least one hydroxyl group, and X and Y are independently a hydrogen atom or an alkyl group having 1 to 6 carbon atoms, which may contain at least one oxygen atom in its structure.

2. The cosmetic skin care composition according to claim 1, wherein the wrinkling modifier and the synthetic sphingosine derivative are contained in amounts of 0.001 to 50% by weight and 0.0001 to 10% by weight, respectively.

3. The cosmetic skin care composition according to claim 1 or 2, which further comprises an organic acid, an inorganic acid or an ester thereof.

4. The cosmetic skin care composition according to claim 3, wherein the organic acid, the inorganic acid or the ester thereof is contained in an amount of 0.001 to 30% by weight.

* * * * *